United States Patent
Semba

(10) Patent No.: US 10,238,359 B2
(45) Date of Patent: Mar. 26, 2019

(54) APPARATUS METHOD MEDIUM FOR SELECTIVE MODIFICATION OF IDENTIFICATION INFORMATION IN AN IMAGING ORDER

(71) Applicant: CANON KABUSHIKI KAISHA, Tokyo (JP)

(72) Inventor: Daiya Semba, Inagi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 656 days.

(21) Appl. No.: 14/220,229

(22) Filed: Mar. 20, 2014

(65) Prior Publication Data

US 2014/0294278 A1 Oct. 2, 2014

(30) Foreign Application Priority Data

Mar. 29, 2013 (JP) ................. 2013-074864

(51) Int. Cl.
*A61B 6/00* (2006.01)
*G06F 19/00* (2018.01)
(Continued)

(52) U.S. Cl.
CPC .............. *A61B 6/563* (2013.01); *A61B 6/468* (2013.01); *A61B 6/5294* (2013.01);
(Continued)

(58) Field of Classification Search
CPC ............. G06F 19/321; G06F 19/3406; G06F 17/30371; A61B 6/468; A61B 6/5294;
(Continued)

(56) References Cited

U.S. PATENT DOCUMENTS

2008/0140947 A1* 6/2008 Slik ................. G06F 3/0605
711/154
2009/0054755 A1* 2/2009 Shiibashi ............. G06F 19/321
600/407

(Continued)

FOREIGN PATENT DOCUMENTS

| JP | 2005-149111 | 6/2005 |
| JP | 2010-026984 | 2/2010 |
| JP | 2011-005169 | 1/2011 |

OTHER PUBLICATIONS

Poolet, M. "SQL by Design: How to Choose a Primary Key." Mar. 31, 1999. Web. Accessed May 12, 2017.*

(Continued)

*Primary Examiner* — Geoffrey E Summers
(74) *Attorney, Agent, or Firm* — Venable LLP

(57) ABSTRACT

There is provided with an imaging control apparatus. A reception unit receives an imaging order. A control unit permits adding identification information if the received imaging order includes no identification information and to inhibit correction of the identification information upon determining that the identification information is included in the imaging order. An obtaining unit obtains information to be added as the identification information if the identification information is not included in the imaging order. A transmission unit transmits an image captured in accordance with the imaging order and either the obtained identification information or the identification information included in the imaging order, in association with each other, to an external image archiving apparatus.

14 Claims, 10 Drawing Sheets

(51) Int. Cl.
  *G16H 30/20* (2018.01)
  *G16H 40/63* (2018.01)
(52) U.S. Cl.
  CPC ............ *G06F 19/321* (2013.01); *G16H 30/20* (2018.01); *G16H 40/63* (2018.01)
(58) Field of Classification Search
  CPC ......... A61B 6/563; A61B 6/566; A61B 6/486; G16H 40/63; G16H 30/20
  USPC ........................................................ 382/305
  See application file for complete search history.

(56) References Cited

U.S. PATENT DOCUMENTS

| | | | |
|---|---|---|---|
| 2010/0023556 A1 | 1/2010 | Sawada et al. | 707/104.1 |
| 2011/0010192 A1* | 1/2011 | Backhaus | G06F 19/321 |
| | | | 705/2 |
| 2011/0110568 A1* | 5/2011 | Vesper | G06F 19/321 |
| | | | 382/128 |
| 2014/0112447 A1 | 4/2014 | Semba | 378/98 |

OTHER PUBLICATIONS

Langer, Steve G., Sue Ramthun, and Claire Bender. "Introduction to digital medical image management: departmental concerns." American Journal of Roentgenology 198.4 (2012): 746-753.*
Huang, H. K. PACS and Imaging Informatics: Basic Principles and Applications. John Wiley and Sons, 2005.*

* cited by examiner

FIG. 3A

| SEARCH: | | | | | |
|---|---|---|---|---|---|
| ● SEARCH FOR ALL ○ SUSPENDED INSPECTION | | | | | |
| STATE | PATIENT ID | PATIENT NAME | SEX | ACCESSION NUMBER | INSPECTION ID | RESERVATION DATE |
| NEW | P000719 | SUZUKI JIRO | MALE | R18949320 | E1893218 | 2013.02.26 |
| NEW | P001352 | TANAKA SAKURA | FEMALE | | E1752637 | 2013.02.26 |
| NEW | P001421 | SATO GORO | MALE | R23158762 | E1485260 | 2013.02.26 |
| NEW | P001508 | SAITO NOBUO | MALE | R85713465 | E1991475 | 2013.02.26 |
| | | | | | | |
| | | | | | | |
| | | | | | | |

PATIENT INFORMATION [EDIT]
PATIENT ID : P001352
PATIENT NAME : TANAKA SAKURA
SEX : FEMALE

INSPECTION INFORMATION [EDIT]
ACCESSION NUMBER :
INSPECTION ID : E1752637

☐ CHEST

[UPDATE] [START INSPECTION]

FIG. 3B

| STATE | PATIENT ID | PATIENT NAME | SEX | ACCESSION NUMBER | INSPECTION ID | RESERVATION DATE |
|---|---|---|---|---|---|---|
| NEW | P000719 | SUZUKI JIRO | MALE | R18949320 | E1893218 | 2013.02.26 |
| NEW | P001352 | TANAKA SAKURA | FEMALE | R00000001 | E1752637 | 2013.02.26 |
| NEW | P001421 | SATO GORO | MALE | R23158762 | E1485260 | 2013.02.26 |
| NEW | P001508 | SAITO NOBUO | MALE | R85713465 | E1991475 | 2013.02.26 |
|  |  |  |  |  |  |  |
|  |  |  |  |  |  |  |
|  |  |  |  |  |  |  |

SEARCH:

● SEARCH FOR ALL ○ SUSPENDED INSPECTION

PATIENT INFORMATION [EDIT]
PATIENT ID : P001352
PATIENT NAME : TANAKA SAKURA
SEX : FEMALE

INSPECTION INFORMATION [EDIT]
ACCESSION NUMBER : R00000001
INSPECTION ID : E1752637

☐ CHEST

[UPDATE] [START INSPECTION]

APPARATUS METHOD MEDIUM FOR SELECTIVE MODIFICATION OF IDENTIFICATION INFORMATION IN AN IMAGING ORDER

BACKGROUND OF THE INVENTION

Field of the Invention

The present invention relates to an imaging control apparatus, an imaging apparatus, a control apparatus for radiation imaging, a method of controlling the imaging control apparatus, a method of controlling the control apparatus for radiation imaging, and a storage medium.

Description of the Related Art

Recently, HIS (Hospital Information Systems) have been constructed in hospitals where apparatuses are connected to each other via a network. When, for example, the operator determines that X-ray imaging is necessary, he/she inputs an inspection instruction from a terminal like an RIS (Radiology Information System) terminal. This inspection instruction is transmitted to a radiology department. This inspection instruction is called an inspection order, which includes inspection information. The inspection information includes, for example, the name of the department of the request source, an inspection item, the individual data of a patient, an inspection ID, and an accession number. Upon reception of the inspection order, the radiology department adds imaging conditions to the inspection order and transfers the order to an X-ray imaging apparatus. The X-ray imaging apparatus executes X-ray imaging in accordance with the received inspection order.

Inspection information is added to the image captured by the X-ray imaging apparatus to make the image identifiable. This image is then transferred to a PACS (Picture Archiving and Communication System) or printed out. The PACS stores, for example, inspection information such as an inspection ID or accession number as a collation key in association with an image. The user can obtain a captured image corresponding to the inspection information input by the user from the PACS.

In order to enable searching for captured images, unique inspection information such as an inspection ID or accession number is added to each captured image stored in the PACS. For this purpose, in general, a unique inspection ID or accession number is also added to an inspection order. However, when the operator inputs an inspection ID or accession number, the PACS may register a wrong inspection ID or accession number due to an input error by the operator. The occurrence of such an error may make it impossible to refer to any captured images recorded on the PACS.

Japanese Patent Laid-Open No. 2005-149111 has proposed a method of, when inputting additional information about a medical image, collating the input information with information recorded on an RIS or medical database. If a mismatch is detected, the operator is presented with correction candidates based on the RIS or medical database.

SUMMARY OF THE INVENTION

According to an embodiment of the present invention, an imaging control apparatus comprises: a reception unit configured to receive an imaging order; a control unit configured to permit adding identification information if the received imaging order includes no identification information and to inhibit correction of the identification information upon determining that the identification information is included in the imaging order; an obtaining unit configured to obtain information to be added as the identification information if the identification information is not included in the imaging order; and a transmission unit configured to transmit an image captured in accordance with the imaging order and either the obtained identification information or the identification information included in the imaging order, in association with each other, to an external image archiving apparatus.

According to another embodiment of the present invention, a control apparatus for controlling radiation imaging comprises: a communication unit configured to communicate with an image archiving apparatus; an obtaining unit configured to obtain identification information based on information obtained from the image archiving apparatus via the communication unit, wherein the obtained identification information differs from identification information of an imaging order corresponding to radiation image data stored in the image archiving apparatus; and a control unit configured to cause the communication unit to transmit image information obtained by associating the obtained identification information with radiation image data obtained by the radiation imaging to the image archiving apparatus.

According to still another embodiment of the present invention, a control method of an imaging control apparatus comprises: receiving an imaging order; permitting adding identification information if the received imaging order includes no identification information; inhibiting correction of the identification information upon determining that the identification information is included in the imaging order; obtaining identification information to be added as the identification information if the identification information is not included in the imaging order; and transmitting an image captured in accordance with the imaging order and either the obtained identification information or the identification information included in the imaging order, in association with each other, to an external image archiving apparatus.

According to yet another embodiment of the present invention, a control method of controlling radiation imaging comprises: communicating with an image archiving apparatus; obtaining identification information based on information obtained from the image archiving apparatus via the communication unit, wherein the obtained identification information differs from identification information of an imaging order corresponding to radiation image data stored in the image archiving apparatus; and causing the communication unit to transmit image information obtained by associating the obtained identification information with radiation image data obtained by the radiation imaging to the image archiving apparatus.

According to still yet another embodiment of the present invention, a non-transitory computer-readable medium stores a program for instructing a computer to perform a method comprising: receiving an imaging order; permitting adding identification information if the received imaging order includes no identification information; inhibiting correction of the identification information upon determining that the identification information is included in the imaging order; obtaining identification information to be added as the identification information if the identification information is not included in the imaging order; and transmitting an image captured in accordance with the imaging order and either the obtained identification information or the identification information included in the imaging order, in association with each other, to an external image archiving apparatus.

According to yet still another embodiment of the present invention, a non-transitory computer-readable medium stores a program for instructing a computer to perform the method comprising: communicating with an image archiving apparatus; obtaining identification information based on information obtained from the image archiving apparatus via the communication unit, wherein the obtained identification information differs from identification information of an imaging order corresponding to radiation image data stored in the image archiving apparatus; and causing the communication unit to transmit image information obtained by associating the obtained identification information with radiation image data obtained by the radiation imaging to the image archiving apparatus.

Further features of the present invention will become apparent from the following description of exemplary embodiments (with reference to the attached drawings).

BRIEF DESCRIPTION OF THE DRAWINGS

FIGS. 3A and 3B are views each showing an example of a display screen indicating a list of inspections planned to be carried out;

DESCRIPTION OF THE EMBODIMENTS

The method disclosed in Japanese Patent Laid-Open No. 2005-149111 is based on the premise that information as correction candidates is registered in an RIS or medical database in advance. This method therefore cannot cope with a case in which the operator forgets to register an inspection ID or accession number or registers wrong information when, for example, needing to quickly perform X-ray imaging for an emergency patient. Assume that a HIS or RIS has an automatic numbering system. Even in this case, when, for example, taking care of an emergency patient, the automatic numbering system may be inactive due to maintenance or the like. In such a case, there is still a possibility that the operator can forget to register an inspection ID or accession number or register wrong information.

Several embodiments are configured to reduce the possibility of failing to add identification information or adding wrong information to a captured image, and suppress the failure to search for a stored captured image.

Embodiments of a radiation imaging system and its processing method of the present invention will be described in detail below with reference to the accompanying drawings. However, the scope of the present invention is not limited to the following embodiments. Each embodiment to be described below uses X-rays as radiation. However, the radiation to be used is not limited to X-rays, but may be, for example, electromagnetic waves, α-rays, β-rays, or γ-rays.

When the operator has forgotten to register inspection information such as an inspection ID or accession number or has registered wrong information in an inspection order, the operator of an X-ray imaging system may find such an event and correct the inspection information. However, the operator of the X-ray imaging system may overlook such an event. In addition, the operator of the X-ray imaging system may erroneously correct inspection information which normally need not be corrected. In these cases as well, since wrong inspection information is added to a captured image, it may not be possible to search for the captured image stored in the PACS. The following embodiments can reduce such possibility.

First Embodiment

Figure 1:
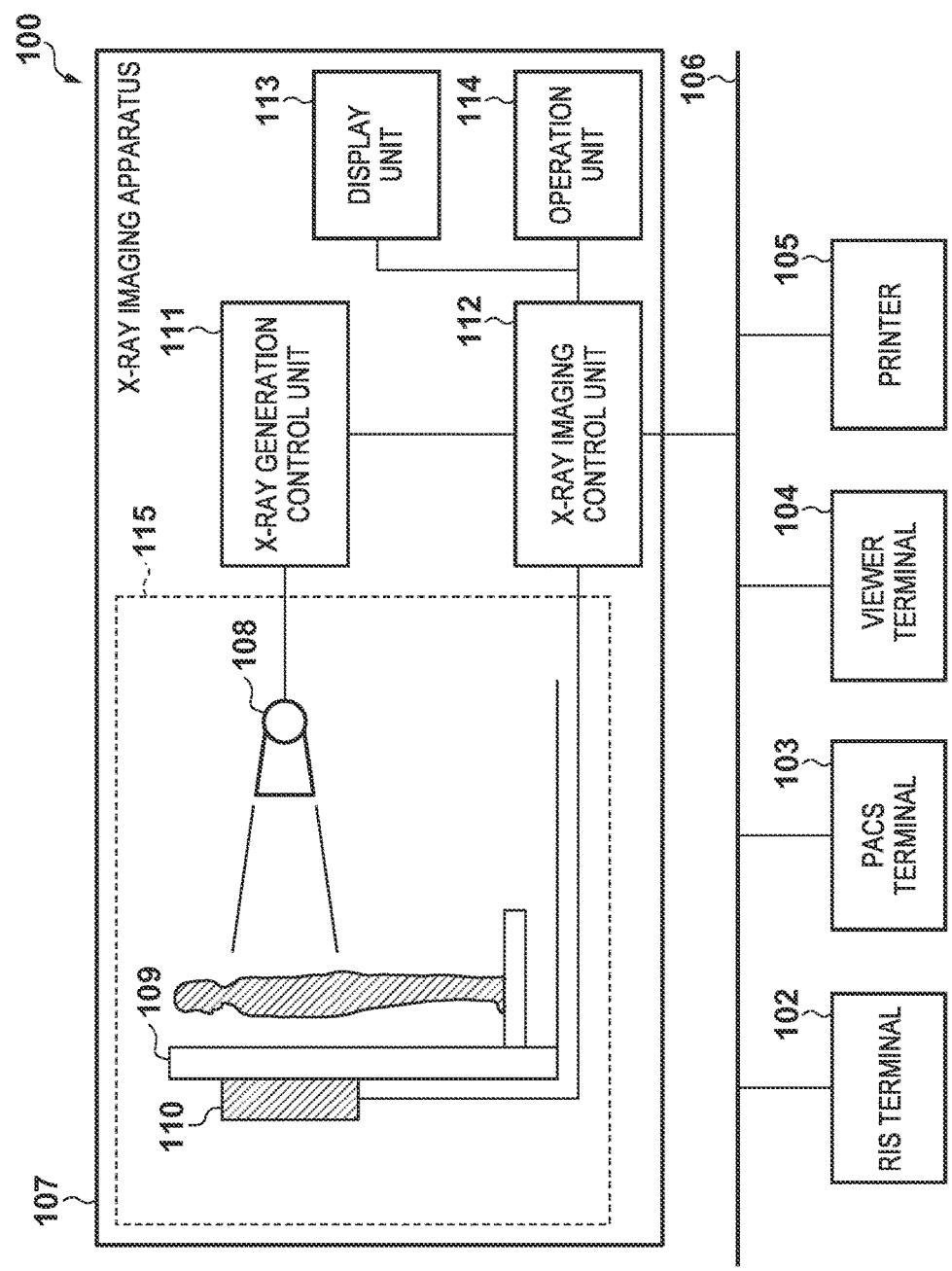
FIG. 1 is a block diagram showing an example of an X-ray imaging system 101 according to the first embodiment.

FIG. 1 shows an X-ray imaging system 101 according to the first embodiment, which is an example of a radiation imaging system according to the present invention. The X-ray imaging system 101 includes an RIS terminal 102, a PACS terminal 103, a viewer terminal 104, a printer 105, and an X-ray imaging apparatus 107. These apparatuses are connected to each other via a communication unit 106 such as a network.

The RIS terminal 102 is an operation terminal connected to the X-ray imaging system 101 and forms an information system in a radiology department. This information system can be, for example, an information management system which comprehensively manages additional information which is information added to radiation images or inspection orders. This additional information can include inspection information including an inspection ID or accession number. The operator can input an inspection order (inspection instruction) via the RIS terminal 102. The X-ray imaging apparatus 107 performs imaging in accordance with this inspection order. Assume that in this embodiment, the RIS terminal 102 stores and manages input inspection orders. However, a server (not shown) connected to the RIS terminal 102 and the X-ray imaging apparatus 107 may store and manage input inspection orders. In another embodiment, the X-ray imaging apparatus 107 may store and manage input inspection orders.

The PACS terminal 103 stores and manages the images captured by the X-ray imaging apparatus 107. That is, the PACS terminal 103 can function as part of the image management system which manages captured images. The viewer terminal 104 can display and output an X-ray image stored in the PACS terminal 103. The printer 105 can print out an X-ray image stored in the PACS terminal 103.

The X-ray imaging apparatus 107 captures an X-ray digital image (to be referred to as a captured image hereinafter). The X-ray imaging apparatus 107 performs inspection (imaging) based on an inspection order including a plurality of pieces of inspection information. Inspection information includes imaging protocol information. Imaging protocols respectively define imaging conditions, the details of image processing executed for captured images, and the like. More specifically, each imaging protocol includes performed imaging information or parameter information used at the time of imaging, image processing, or the like, and imaging environment information such as a sensor type and an imaging posture. In addition, inspection information includes information specifying an inspection order such as an inspection ID and an accession number or information specifying a captured image based on an inspection order.

The X-ray imaging apparatus 107 includes an imaging unit 115, an X-ray generation control unit 111, an X-ray imaging control unit 112, a display unit 113, and an operation unit 114. The imaging unit 115 includes an X-ray tube 108, a sensor unit 109, and a sensor 110. The X-ray tube 108 functions as a radiation generation unit. That is, the X-ray tube 108 irradiates an object (that is, a subject) with X-rays. The sensor 110 functions as radiation detection unit. That is, the sensor 110 detects X-rays transmitted through a subject as charges corresponding to the amount of transmitted X-rays. The sensor unit 109 generates a captured image by A/D-converting the charges detected by the sensor 110. The sensor unit 109 then transfers the captured image to the X-ray imaging control unit 112.

The X-ray generation control unit 111 controls the generation of X-rays based on an imaging protocol under the control of the X-ray imaging control unit 112. More specifically, the X-ray generation control unit 111 generates X-rays by applying a voltage to the X-ray tube 108 in accordance with imaging conditions (for example, parameters such as a tube current, a tube voltage, and an irradiation time) corresponding to an imaging protocol.

The X-ray imaging control unit 112 comprehensively controls X-ray imaging processing based on the imaging protocol. In addition, the X-ray imaging control unit 112 performs image processing for the captured image obtained from the imaging unit 115. Image processing includes correction processing, tone processing, and frequency processing. The X-ray imaging control unit 112 performs image processing by using the image processing parameters based on the imaging protocol. In addition, the X-ray imaging control unit 112 can transmit the obtained captured image to an external apparatus such as the PACS terminal 103 or the printer 105. Upon receiving the captured image, the PACS terminal 103 stores the received captured image together with inspection information for identifying the captured image. This inspection information can be, for example, the inspection ID or accession number added to the inspection order. The PACS terminal 103 may store the inspection order in association with the captured image.

The display unit 113 displays information such as a system state to the operator. The display unit 113 can be, for example, a display. The display unit 113 can display, for example, the inspection order received from the RIS terminal 102 or the inspection order generated by the operator of the X-ray imaging apparatus 107. The operation unit 114 obtains an instruction from the operator. The operation unit 114 can be, for example, a keyboard, a mouse, or various types of buttons. For example, the operator can input an image copy instruction to the X-ray imaging apparatus 107 via the operation unit 114.

An example of the functional arrangement of the X-ray imaging control unit 112 for implementing the first embodiment will be described next with reference to FIG. 2. The X-ray imaging control unit 112 includes an inspection order obtaining unit 201, an inspection order storage unit 202, an image obtaining unit 203, an inspection information output unit 204, an correction determination unit 205, an information correction unit 208, and an correction inhibition unit 209. These units are connected to each other via a system bus 210.

The inspection order obtaining unit 201 obtains an inspection order from an external system such as the RIS terminal 102 (obtains an inspection instruction). As described above, the inspection order includes a plurality of pieces of inspection information, for example, patient information indicating a patient to be imaged, imaging details information constituted by a plurality of imaging protocols, and information identifying the inspection order. The inspection order storage unit 202 stores the inspection order obtained by the inspection order obtaining unit 201. Storing the inspection order in the inspection order storage unit 202 enables to refer to the obtained inspection order even when the X-ray imaging apparatus 107 becomes offline.

The image obtaining unit 203 obtains a captured image from the imaging unit 115. The image obtaining unit 203 may obtain a captured image via a network or obtain a captured image via a medium such as a CD-ROM or DVD. The inspection information output unit 204 transfers a captured image, inspection information, and the like to the display unit 113 or an external apparatus such as the PACS terminal 103 or the printer 105.

The correction determination unit 205 determines whether to correct inspection information. The correction determination unit 205 includes a non-input determination unit 206 and a duplication determination unit 207. The non-input determination unit 206 determines whether there is any item in which no inspection information has been input. The duplication determination unit 207 determines whether a unique item (an accession number, inspection ID, or the like), duplication of which is not allowed, coincides with another inspection order registered in the X-ray imaging system 101 or inspection information about a captured image. In this embodiment, this unique item is used as identification information identifying the image captured in accordance with an inspection order, and is stored in the PACS terminal 103 in association with the captured image. The duplication determination unit 207 can determine the duplication of identification information. Such a unique item can be, for example, an ID identifying an inspection order such as the accession number of the inspection order or an inspection ID.

For example, the duplication determination unit 207 can determine whether the inspection ID included in an inspection order is duplicative with the inspection ID associated with the captured image registered in the PACS terminal 103. Alternatively, the duplication determination unit 207 may determine whether the inspection ID included in an inspection order is duplicative with the inspection ID included in the inspection order registered in the RIS terminal 102. It is possible to configure which items are to be examined regarding whether no information has been input to the item or the item is duplicative, in advance.

If the correction determination unit 205 determines that inspection information should be corrected, the information correction unit 208 corrects the inspection information in accordance with an input operation by the operator. If the correction determination unit 205 determines that inspection information should not be corrected, the correction inhibition unit 209 inhibits correction of the inspection information.

Figure 2:
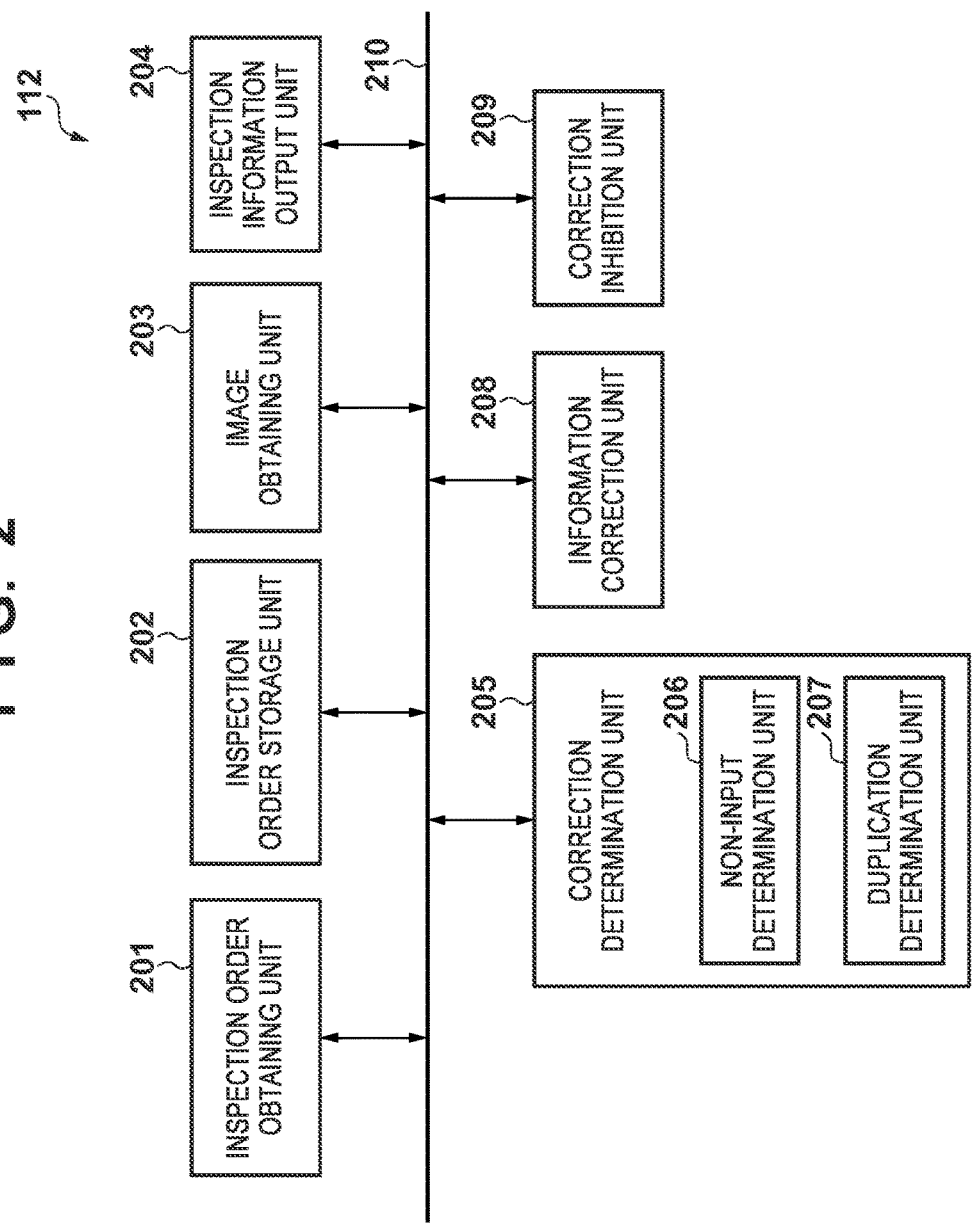
FIG. 2 is a block diagram showing an example of the functional arrangement of an X-ray imaging control unit 112 according to the first embodiment.

Each unit of the X-ray imaging apparatus 107 shown in FIGS. 1 and 2 may be implemented by dedicated hardware. At least some of the units of the X-ray imaging apparatus 107 shown in FIGS. 1 and 2 may be implemented by computer programs. That is, a computer including a processor and a memory obtains programs via a storage medium or network. The processor then operates in accordance with the programs loaded in the memory to implement the operations of the respective units of the X-ray imaging apparatus 107.

Figure 4:
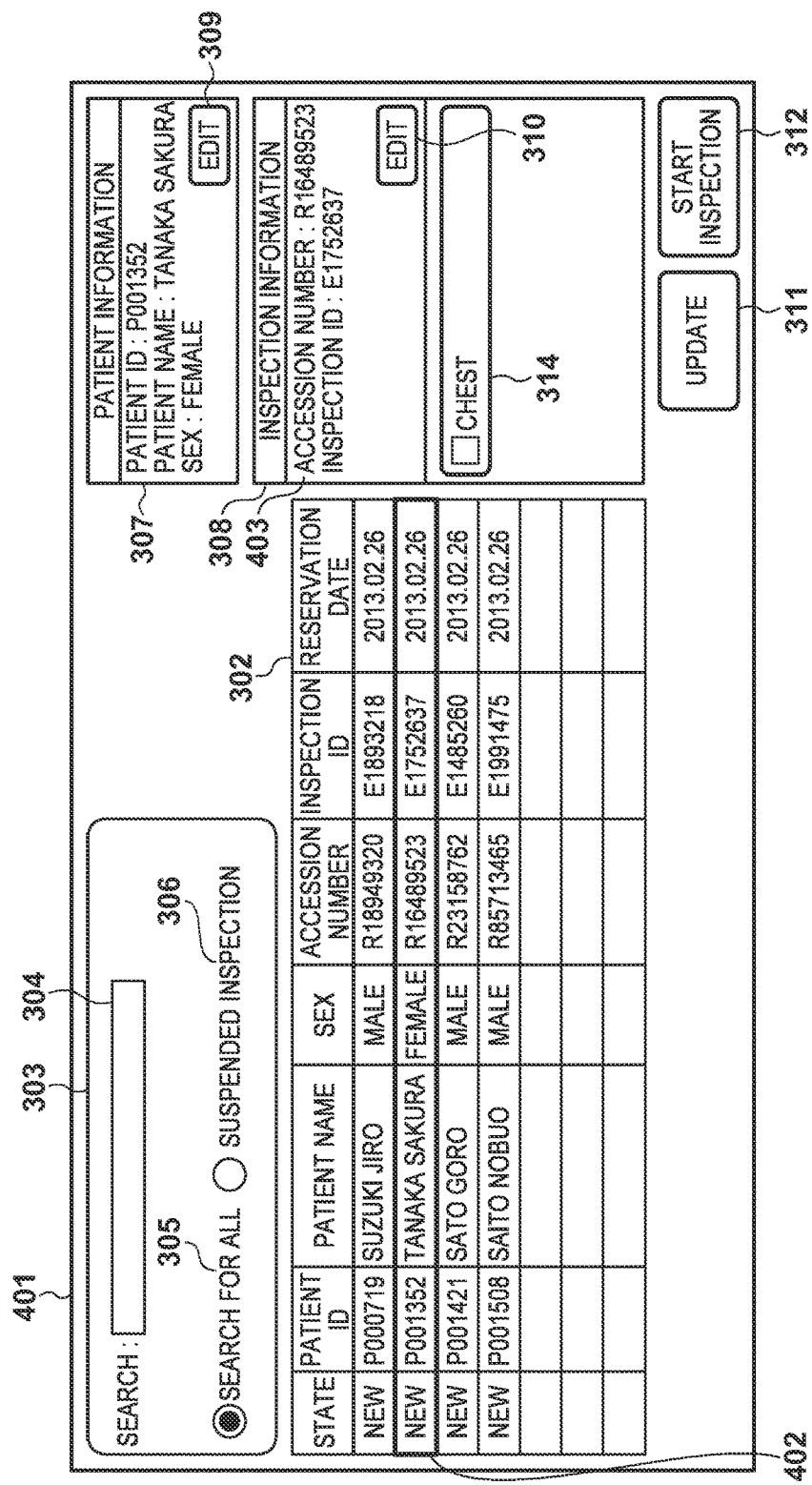
FIG. 4 is a view showing an example of a display screen indicating a list of inspections planned to be carried out.

FIGS. 3A and 4 each show a display example on the display unit 113. FIG. 3A shows a display screen 301 indicating a list of inspections planned to be carried out before the correction of an accession number. FIG. 4 shows a display screen 401 indicating a list of inspections planned to be carried out after the correction of the accession number. Referring to FIGS. 3A and 4, an inspection list 302 displays a list of inspection information about an inspection order in an execution plan.

Inputting a value in a search keyword input box 304 in a search area 303 can narrow down inspection information to be displayed in the inspection list 302. It is possible to narrow down inspection information to be displayed in the inspection list 302 based on inspection information indicating an inspection state by using a radio button 305 which designates all inspections and a radio button 306 which designates a suspended inspection.

When the operator selects an inspection order with the inspection list 302, the apparatus displays the inspection information included in the selected inspection order. In this embodiment, the apparatus displays patient information, of inspection information, which indicates a patient in a patient information display portion 307, and displays the remaining information in an inspection information display portion 308. Pressing an editing button 309 in the patient information display portion 307 can edit the patient information displayed in the patient information display portion 307. In addition, pressing an editing button 310 in the inspection information display portion 308 can edit the inspection information displayed in the inspection information display portion 308. Pressing an update button 311 can update the information to be displayed in the inspection list 302 to a latest state. Pressing an inspection start button 312 can start the inspection selected from the inspection list 302.

Figure 5:
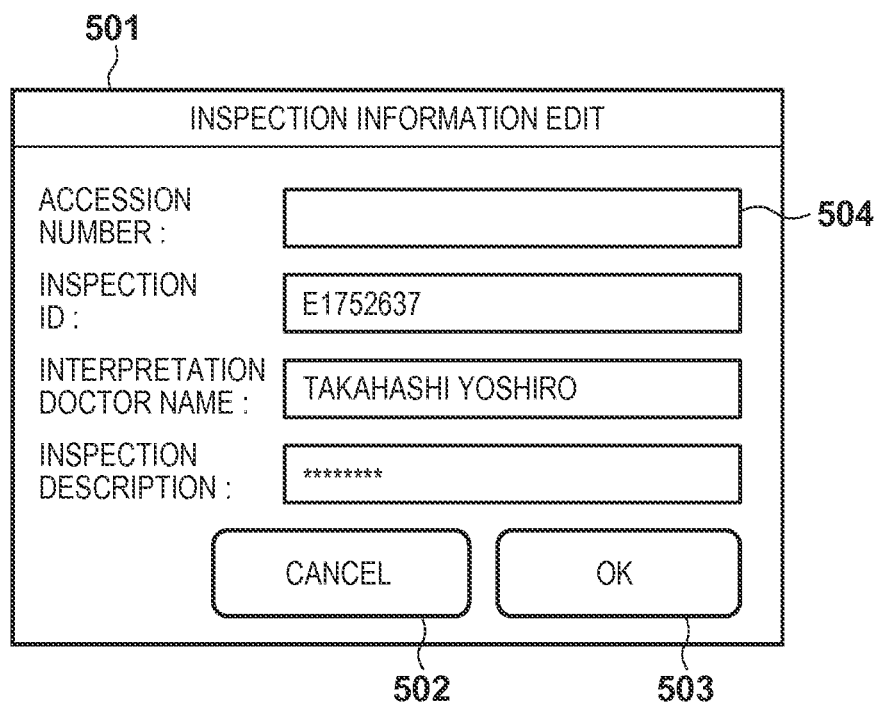
FIG. 5 is a view showing an example of an information editing screen.

FIG. 5 shows an information editing screen 501 displayed upon pressing of the editing button 310. The information editing screen 501 displays each item of the inspection information displayed in the inspection information display portion 308. The operator can edit each item of the inspection information displayed on the information editing screen 501 in accordance with the processing shown in FIG. 6. Pressing a cancel button 502 can discard editing details. Pressing an OK button 503 can update the inspection information included in an inspection order selected in accordance with editing details.

Figure 6:
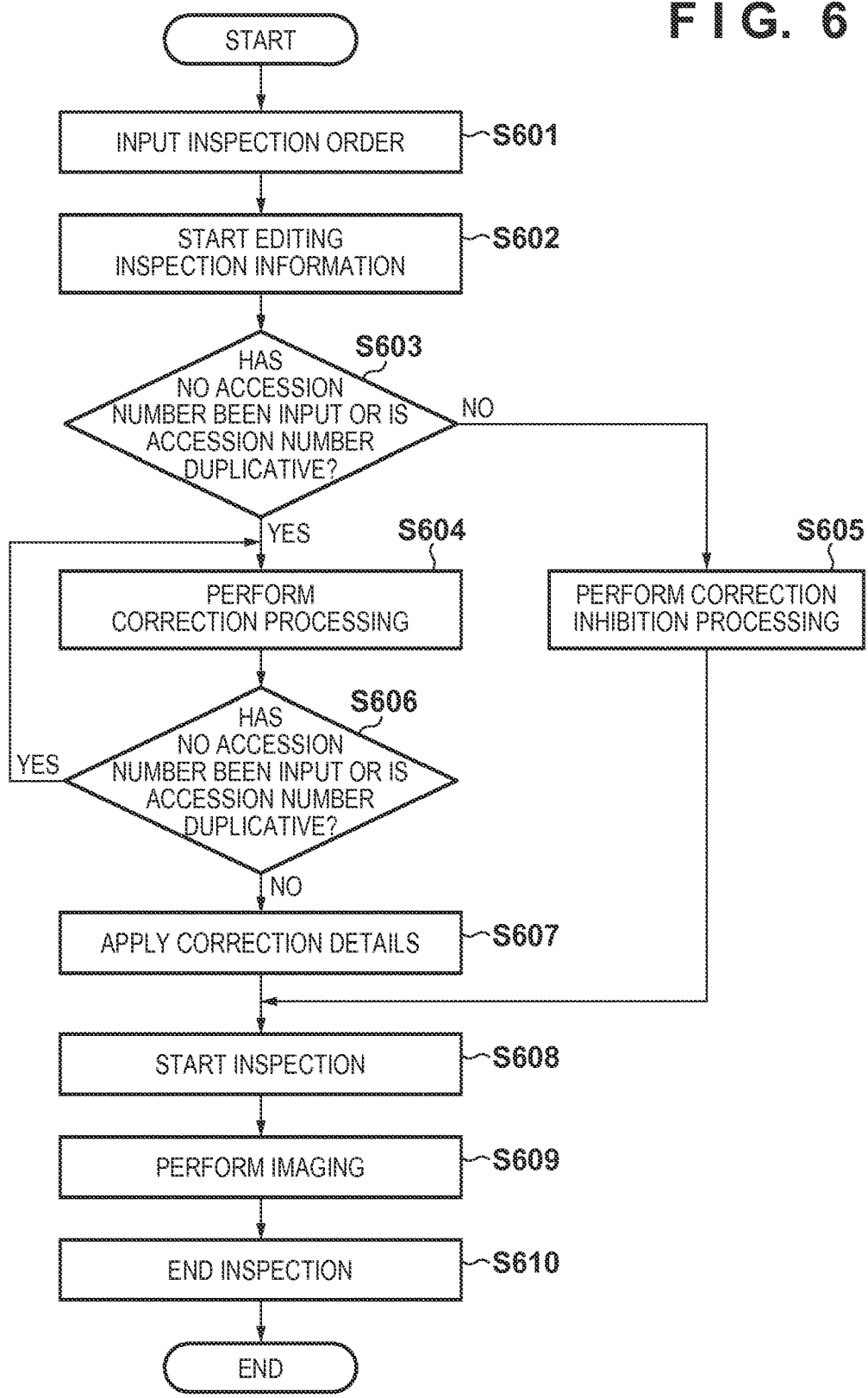
FIG. 6 is a flowchart showing an example of processing in the first embodiment.

An example of a series of processing from the start of an inspection upon obtaining inspection information to the end of the inspection in the first embodiment will be described in detail below with reference to FIG. 6. In step S601, the inspection order obtaining unit 201 obtains an inspection order from the RIS terminal 102. In this case, the inspection order obtaining unit 201 may obtain the inspection order manually generated by the operator via the operation unit 114. The inspection order storage unit 202 stores the obtained inspection order. The inspection order stored in the inspection order storage unit 202 is displayed as the inspection list 302 on the display screen 301 of the display unit 113.

In step S602, the operator selects an inspection order from the inspection list 302. According to this description, the operator selects an inspection order 313 to start an inspection based on the inspection order 313. At the time of the selection, the apparatus displays the patient information included in the inspection order 313 in the patient information display portion 307, and displays the inspection information included in the inspection order 313 in the inspection information display portion 308. In addition, the apparatus displays an imaging protocol 314 included in the inspection order 313 in the inspection information display portion 308.

Assume that in the following description, the operator has noticed that no accession number is displayed in an accession number field 315 of the inspection information display portion 308, that is, no accession number has been input. Assume that the apparatus has performed imaging without any accession number being input and has transferred inspection information and imaging information to the PACS terminal 103. In this case, since no accession number matches the captured image, there is a possibility of failing to refer to the captured image, captured in accordance with the inspection order 313, in the PACS terminal 103. For this reason, when the operator presses the editing button 310 via the operation unit 114, the display unit 113 displays the information editing screen 501. As indicated by a display screen 801 in FIG. 3B, the operator may notice that the accession number displayed in an accession number field 403 of the inspection information display portion 308 coincides with an accession number already registered in the PACS terminal with regard to an inspection order 402. Even in this case, the operator may press the editing button 310 via the operation unit 114.

In step S603, the correction determination unit 205 determines whether to correct the inspection information. The non-input determination unit 206 and the duplication determination unit 207 perform this determination. If no accession number has been input concerning the selected inspection order 313, that is, the inspection order 313 includes no accession number, the non-input determination unit 206 determines that an accession number should be corrected. In addition, if the accession number of the inspection order 313 coincides with an accession number corresponding to a captured image recorded on the PACS terminal 103, the duplication determination unit 207 determines that the accession number should be corrected. In this embodiment, if at least one of the non-input determination unit 206 and the duplication determination unit 207 determines that the inspection information should be corrected, the correction determination unit 205 determines that the inspection information should be corrected. If the correction determination unit 205 determines that the inspection information should be corrected, the process advances to step S604. If the correction determination unit 205 determines that the inspection information should not be corrected, the process advances to step S605. If the process advances to step S605, the information correction unit 208 does not obtain the user input indicating the accession number. The correction determination unit 205 may perform the above determination for a plurality of items of inspection information. In this case, if inspection information concerning at least one of the items should be corrected, the process advances to step S604.

In step S604, the information correction unit 208 permits to input to an input box 504 on the information editing screen 501 to edit the accession number. At this time, the information correction unit 208 causes the display unit 113 to display a message (not shown) prompting to input an accession number to the input box 504 or correct the accession number in the input box 504. The operator inputs an accession number to the input box 504 via the operation unit 114 (information obtaining). In addition, to reflect the correction, the operator presses the OK button 503 via the operation unit 114. The process then advances to step S606.

In step S606, the correction determination unit 205 determines again whether to correct the inspection information. The correction determination unit 205 can perform this determination in the same manner as in step S603. If the correction determination unit 205 determines that the inspection information should be corrected, the process returns to step S604. If the correction determination unit 205 determines that the inspection information should not be corrected, the process advances to step S607. A user input is repeatedly obtained until the correction determination unit 205 determines in step S606 that the inspection information should not be corrected, and the user inputs an accession number which does not coincides with any of the accession numbers corresponding to the captured images recorded on the PACS terminal 103. The processing in step S606 enables to further check inspection information for identifying an inspection of an inspection ID, accession number, and the like, so as to avoid it from being duplicative. This makes it possible to further reduce the possibility of coincidence between an inspection ID or accession number after correction and an inspection ID or accession number corresponding to another captured image already registered in the PACS when the operator of the X-ray imaging system has manually corrected the inspection information. As a consequence, it is possible to reduce the possibility of confusion between an obtained captured image and a captured image of a different patient.

In step S607, the information correction unit 208 updates the inspection information of the inspection order 313 stored in the inspection order storage unit 202 in accordance with the information input in step S604. Thereafter, the inspection information output unit 204 causes the display unit 113 to display the display screen 401 including the updated inspection information. More specifically, the inspection information output unit 204 reads out an inspection order from the inspection order storage unit 202 and displays the inspection order on the inspection list 302. The inspection order 402 shown in FIG. 4 is identical to the inspection order 313 in FIG. 3A except that an accession number is added in step S604. In addition, the display in the accession number field 403 is updated in accordance with an input accession number.

In step S605, the correction inhibition unit 209 inhibits input to the input box 504 on the information editing screen 501. That is, the correction inhibition unit 209 does not accept any correction of an accession number via the operation unit 114. At this time, the correction inhibition unit 209 can control a GUI so as to indicate the operator that no input is accepted. For example, the correction inhibition unit 209 changes the color of the input box 504. In addition, the correction inhibition unit 209 can cause the display unit 113 to display a message (not shown) indicating that no input is accepted. Since there is no need to correct the accession number, the operator presses the cancel button 502 or the OK button 503 via the operation unit 114. The display unit 113 then displays the display screen 301 indicating inspections planned to be carried out. Thereafter, the process advances to step S608.

In step S608, the operator presses the inspection start button 312 via the operation unit 114. The apparatus then starts an inspection in accordance with the inspection order selected in this manner. At this time, the display unit 113 can display an imaging screen (not shown) indicating statuses in imaging. In step S609, the operator presses an irradiation button (not shown). The imaging unit 115 is controlled to capture an image of an object in accordance with the inspection order, and performs X-ray imaging of the object. The image obtaining unit 203 obtains the image captured by the imaging unit 115. The image obtaining unit 203 then performs image processing for the obtained captured image, and records the resultant image on the inspection order storage unit 202 in association with the inspection information. As described above, if the correction determination unit 205 determines in step S603 that the inspection information should be corrected, the inspection information includes the accession number obtained in step S604. In addition, if the correction determination unit 205 determines in step S603 that the inspection information should be corrected, the inspection information includes an accession number included in the inspection order obtained in step S601.

In step S610, the operator issues an inspection end instruction via the operation unit 114. Upon receiving the inspection end instruction, the inspection information output unit 204 transfers the captured image stored in the inspection order storage unit 202, associated inspection information and image information, and the like to an external apparatus such as the PACS terminal 103 or the printer 105. The apparatus ends the inspection in this manner.

As described above, the first embodiment enables to input inspection information in the X-ray imaging apparatus when inspection information included in an inspection order, such as an accession number, has not been input due to forgetting to register or the like. This can prevent the failure to refer to captured images in the PACS terminal 103. If inspection information such as an accession number has already been input, the apparatus inhibits the correction of the inspection information. This can prevent the failure to refer to captured images in the PACS terminal 103 due to unnecessary correction. As described above, it is also possible to determine whether to permit the correction of inspection information, depending on whether the inspection information included in an inspection order such as an accession number coincides with any of the inspection information registered in the PACS terminal 103.

Second Embodiment

An X-ray imaging system according to the second embodiment will be described next. An X-ray imaging system 101 according to the second embodiment has the same arrangement as that in the first embodiment shown in FIG. 1. In addition, an X-ray imaging control unit 112 in the second embodiment has the same arrangement as that in the first embodiment shown in FIG. 2. In addition, display screens 301, 401, and 501 indicating inspections planned to be carried out, which are displayed on a display unit 113, can be the same as those in the first embodiment which are shown in FIGS. 3A and 3B, 4, and 5. The differences between the first and second embodiments will be mainly described below, and a description of the same points will be omitted.

Figure 7:
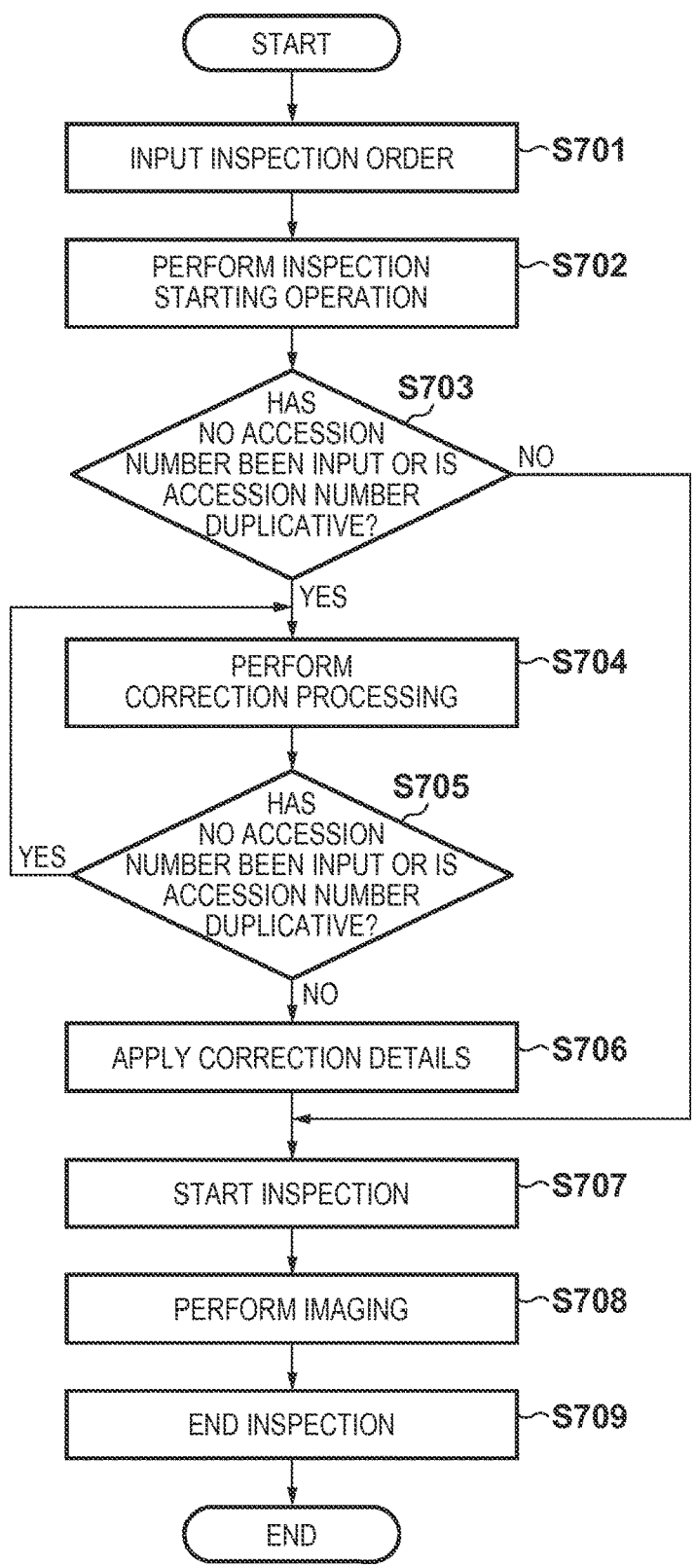
FIG. 7 is a flowchart showing an example of processing in the second embodiment.

An example of a series of processing from the start of an inspection upon obtaining inspection information to the end of the inspection in the second embodiment will be described in detail below with reference to FIG. 7. Step S701 is the same as step S601 in the first embodiment. In step S702, the operator selects an inspection order 313 from an inspection list 302 via an operation unit 114. Subsequently, the operator presses an inspection start button 312.

In step S703, a correction determination unit 205 determines whether to correct the inspection information of the inspection order 313. The correction determination unit 205 performs this determination in the same manner as in step S603 in the first embodiment. If the correction determination unit 205 determines that the inspection information should be corrected, the information correction unit 208 causes the display unit 113 to display the information editing screen 501. The process then advances to step S704. If the correction determination unit 205 determines that the inspection information should not be corrected, a correction inhibition unit 209 inhibits the correction of the inspection information. The process then advances to step S707.

The processing in step S704 is the same as that in step S604 in the first embodiment. The processing in step S705 is also the same as that in step S606 in the first embodiment. If the correction determination unit 205 determines that the inspection information should not be corrected, the process advances to step S706. If the correction determination unit 205 determines that the inspection information should be corrected, the process returns from step S704.

In step S706, an information correction unit 208 updates the inspection information of the inspection order 313 stored in an inspection order storage unit 202 in accordance with the information input in step S704. Thereafter, in step S707, the apparatus starts an inspection based on the selected inspection order. At this time, as in the first embodiment, the display unit 113 may display an imaging screen (not shown) indicating statuses in imaging. The processing in steps S708 and S709 is the same as that in steps S609 and S610 in the first embodiment.

As described above, the second embodiment is configured to prompt to input inspection information at the start of an inspection even if inspection information included in an inspection order, such as an accession number, has not been input or is duplicative due to forgetting to register or the like. This can prevent the failure to input inspection information or duplicative input, and hence the failure to refer to captured images in a PACS terminal 103. In addition, if inspection information such as an accession number has already been input and is not duplicative with any of the inspection information registered in the PACS terminal 103, the apparatus can start an inspection without inputting inspection information. This makes it possible to prevent the failure to refer to captured images in the PACS terminal 103 due to unnecessary correction.

Modifications of First and Second Embodiments

The information correction unit 208 may newly issue (generate) inspection information to be used for updating instead of updating the inspection information of the inspection order 313 in accordance with the information input by the user as in the first and second embodiments. It is possible to implement such an arrangement by correcting the operation in step S604 or S704 in the following manner. That is, if the correction determination unit 205 determines that inspection information concerning a predetermined item such as an accession number should be corrected, the information correction unit 208 obtains inspection information registered in the PACS terminal 103 concerning the correction target item. The information correction unit 208 then newly issues unique information which does not coincide with any of the inspection information registered in the PACS terminal 103. The information correction unit 208 can update the inspection information of the inspection order 313 with the inspection information newly issued in this manner.

This modification enables to automatically obtain non-duplicative inspection information, and hence can prevent the failure to refer to captured images in the PACS terminal 103. When inspection information such as an accession number included in an inspection order has not been input or is duplicative, in particular, the modification enables to more easily update inspection information.

This modification is configured to automatically obtain inspection information such as an accession number included in an inspection order when inspection information has not been input or is duplicative. However, the apparatus may always perform this automatic obtaining operation. In this case as well, it is possible to obtain the effect of preventing the failure to refer to captured images in the PACS terminal 103.

Third Embodiment

Figure 8:
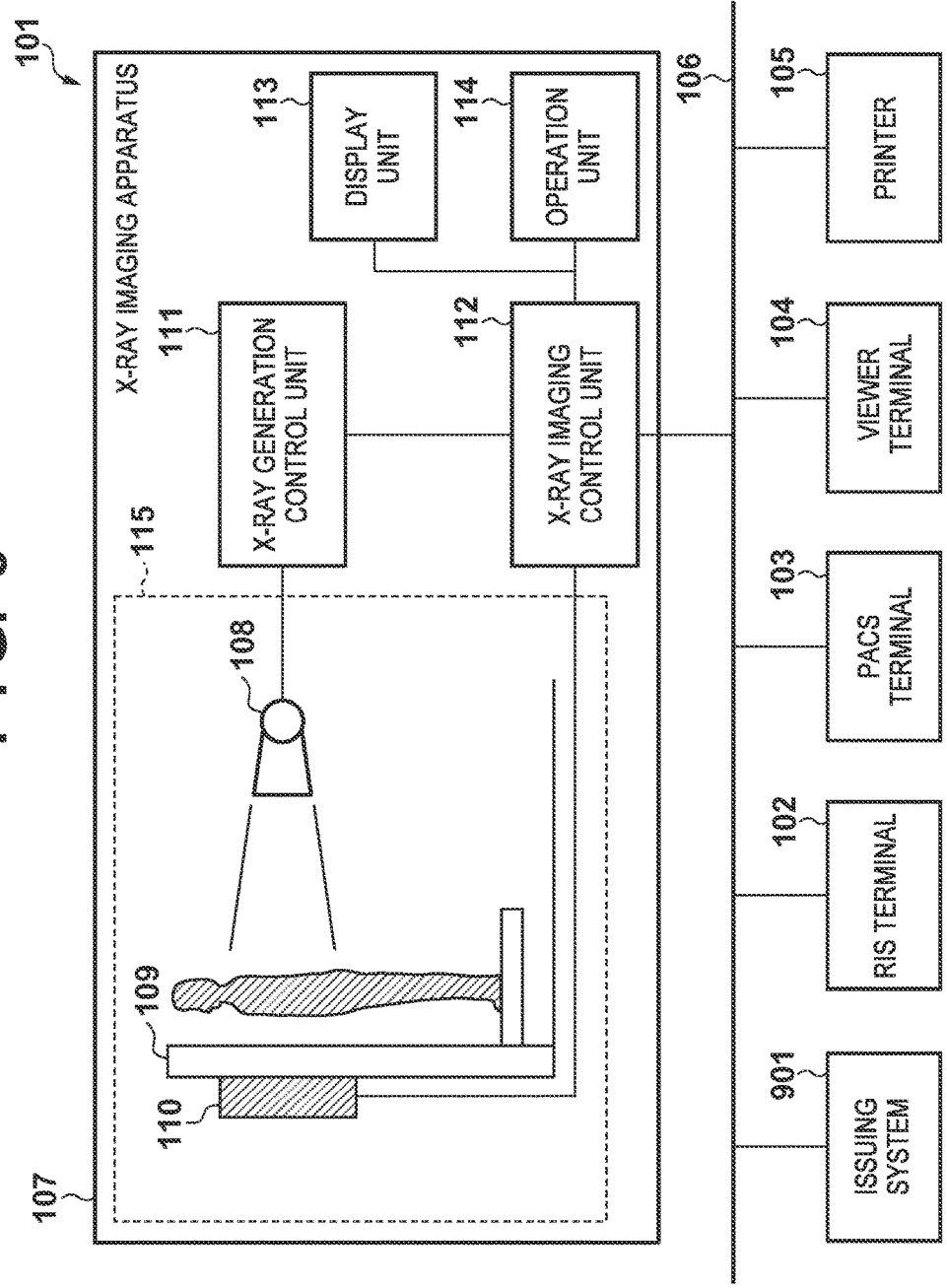
FIG. 8 is a block diagram showing an example of an X-ray imaging system 101 according to the third embodiment.

An X-ray imaging system according to the third embodiment will be described next. FIG. 8 shows an example of the arrangement of an X-ray imaging system 101 according to the third embodiment. The arrangement of the X-ray imaging system 101 according to the third embodiment is similar to that in the first embodiment shown in FIG. 1 except that it includes an issuing system 901. In addition, an X-ray imaging control unit 112 in the third embodiment has the same arrangement as that in the first embodiment shown in FIG. 2. Furthermore, display screens 301, 401, and 501 indicating inspections planned to be carried out, which are displayed on a display unit 113, can be the same as those in the first embodiment which are shown in FIGS. 3A and 3B, 4, and 5. The differences between the first and third embodiments will be described below, and a description of the same points will be omitted. The same reference numerals as in FIG. 1 denote the same components in FIG. 8.

The issuing system 901 can issue inspection information. More specifically, the issuing system 901 can issue unit information which is not permitted to be duplicative in the X-ray imaging system 101, such as an inspection ID, a patient ID, and an accession number, so as to prevent the information from being duplicative. For example, the issuing system 901 may be a numbering system, and can issue information while preventing it from being duplicative by communicating with another apparatus in the X-ray imaging system 101, such as an RIS terminal 102 or a PACS terminal 103. The RIS terminal 102 or an information management system including the RIS terminal 102 may include the issuing system 901.

In this embodiment, if a correction determination unit 205 determines whether the inspection information should be corrected, an information correction unit 208 requests the issuing system 901 to newly issue information concerning the inspection information to be corrected. The information correction unit 208 then updates the inspection information of the inspection order with the information obtained from the issuing system 901.

An example of a series of processing from the start of an inspection upon obtaining inspection information to the end of the inspection in the third embodiment will be described in detail below with reference to FIG. 6. Processing in the third embodiment is similar to that in the first embodiment, and the differences between the first and third embodiments will be described below.

Before the start of step S601, the operator inputs an inspection order to the RIS terminal 102. At this time, the RIS terminal 102 requests the issuing system 901 to issue unique information of inspection information, such as an accession number. The issuing system 901 then issues requested information to the RIS terminal 102. On the RIS terminal 102 side, the operator inputs an inspection order while referring to the information issued by the issuing system 901.

Assume that in this embodiment, although the issuing system 901 has issued an accession number, the operator forgets to input the accession number to an inspection order. This embodiment can also be applied to a case in which although the issuing system 901 has issued an accession number, the operator inputs a wrong accession number to the inspection order, that is, inputs an accession number which has already been registered in the PACS terminal 103. Assume that the inspection order obtaining unit 201 has obtained this inspection order in step S601, and the operator has selected this inspection order in step S602.

In step S604, the information correction unit 208 requests the issuing system 901 to issue new information concerning inspection information to be corrected. In this description, the information correction unit 208 issues a new accession number. In this manner, the information correction unit 208 can obtain an accession number which does not coincide with any of the accession numbers added to the captured images which have already been stored, by communicating with the image management system including the issuing system 901 and the PACS terminal 103. The information correction unit 208 then inputs the obtained accession number to an input box 504. In this embodiment, the process may skip step S606 and advance to step S607 without waiting for input from the user, after the information correction unit 208 obtains an accession number. In this case, the information correction unit 208 updates the inspection information of the inspection order 313 with the obtained accession number.

As described above, according to the third embodiment, it is possible to automatically obtain a non-duplicative inspection information, when inspection information such as an accession number included in an inspection order has not been input or is duplicative. This makes it possible to more easily update inspection information.

Fourth Embodiment

An X-ray imaging system according to the fourth embodiment will be described next. An X-ray imaging system 101 according to the fourth embodiment has the same arrangement as that in the third embodiment shown in FIG. 8. In addition, an X-ray imaging control unit 112 in the fourth embodiment has the same arrangement as that in the third embodiment shown in FIG. 2. Furthermore, display screens 301, 401, and 501 indicating inspections planned to be carried out, which are displayed on a display unit 113, can be the same as those in the third embodiment which are shown in FIGS. 3A and 3B, 4, and 5. The differences between the third and fourth embodiments will be described below, and a description of the same points will be omitted.

Processing in the fourth embodiment will be described with reference to FIG. 7. Before the start of step S701, the operator inputs an inspection order to an RIS terminal 102, as in the third embodiment. Assume that as in the third embodiment, although an issuing system 901 has issued an accession number, the operator has forgotten to input the accession number to an inspection order or has erroneously input a duplicative accession number to the inspection order.

Steps S701 and S702 and steps S704 to S709 are the same as those in the second embodiment. Assume that in step S701, an inspection order obtaining unit 201 has obtained an inspection order to which no accession number has been input. Assume also that in step S702, the operator has selected this inspection order.

In step S704, an information correction unit 208 obtains a new accession number from the issuing system 901 as in step S604 in the third embodiment. Thereafter, in step S706, the information correction unit 208 updates the inspection information of the inspection order 313 stored in an inspection order storage unit 202 in accordance with the information obtained in step S704 as in the second embodiment. As in the third embodiment, after the information correction unit 208 obtains an accession number, the process may skip step S705 and advance to step S706 without waiting for input from the user.

As described above, according to the fourth embodiment, it is possible to automatically obtain a non-duplicative inspection information, when inspection information such as an accession number included in an inspection order has not been input or is duplicative at the start of an inspection. This makes it possible to more easily update inspection information.

Modifications of Third and Fourth Embodiments

In the third and fourth embodiments, the information correction unit 208 requests the issuing system 901 to newly issue information concerning inspection information as a correction target. If, however, the X-ray imaging apparatus 107 cannot communicate with the issuing system 901, the information correction unit 208 cannot request the issuing system 901 to newly issue information. In this modification, the information correction unit 208 determines whether the X-ray imaging apparatus 107 can communicate with the issuing system 901. If no connection is established between them, the information correction unit 208 newly issues inspection information to be used for updating. A description of the same arrangement and processing as those in the third and fourth embodiments will be omitted below.

As in the third and fourth embodiments, before the start of step S601 or S701, the operator inputs an inspection order to the RIS terminal 102. At this time, if connection has been established between the RIS terminal 102 and the issuing system 901 to enable communication between them, the operator inputs an inspection order while referring to the information issued by the issuing system 901. In contrast, in some case, no connection has been established between the RIS terminal 102 and the issuing system 901 to disable communication between them because, for example, the issuing system 901 does not function or exit. In such a case, the operator inputs an inspection order upon determining an inspection ID, a patient ID, accession number, or the like based on a management record book or the like. Assume that as in the third and fourth embodiments, the operator has forgotten to input an accession number to an inspection order or has erroneously input a duplicative accession number to the inspection order.

Figure 9:
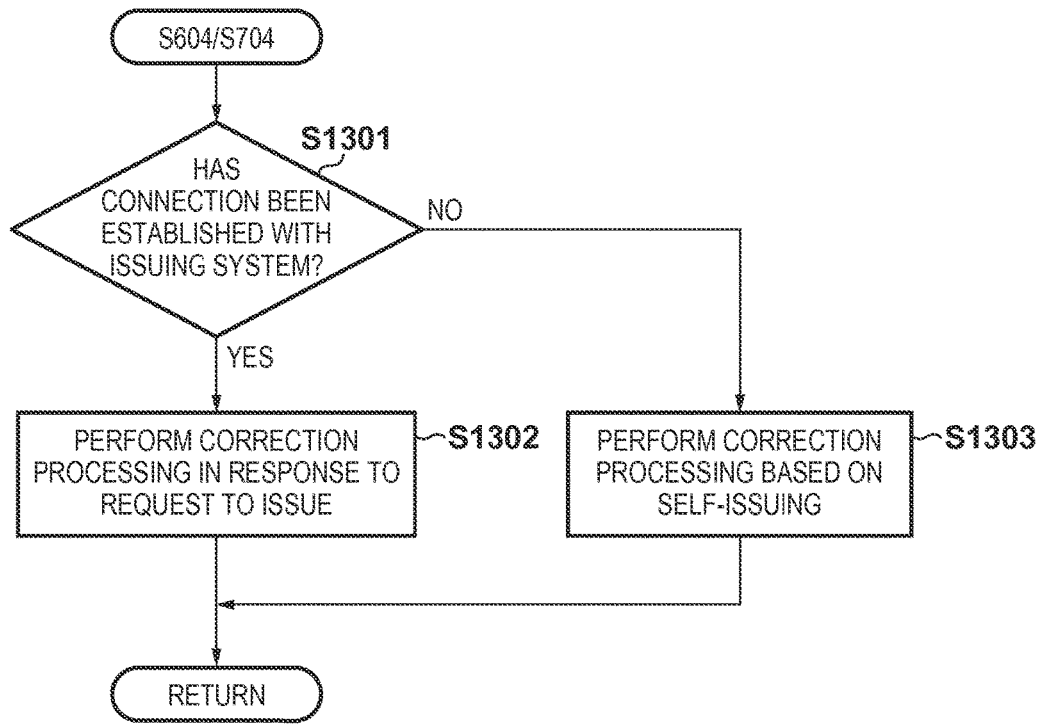
FIG. 9 is a flowchart showing an example of processing in modifications of the third and fourth embodiments.

In this modification, the apparatus performs processing in step S604 or S704 in accordance with the flowchart shown in FIG. 9. In step S1301, the information correction unit 208 determines whether connection has been established between the X-ray imaging apparatus 107 and the issuing system 901. If connection has been established, the process advances to step S1302. If no connection has been established, the process advances to step S1303.

The apparatus performs processing in step S1302 in the same manner as in step S604 or S704 in the third and fourth embodiments, and the information correction unit 208 obtains new inspection information from the issuing system 901. The apparatus performs processing in step S1303 in the same manner as in the modifications of the first and second embodiments, and newly issues inspection information to be used for updating by referring to the inspection information registered in the PACS terminal 103. The information correction unit 208 can update the inspection information of the inspection order 313 by using the inspection information obtained in step S1302 or S1303.

According to this modification, when inspection information such as an accession number included in an inspection order has not been input or is duplicative, it is possible to automatically obtain a non-duplicative inspection information, even if no connection has been established with the issuing system 901. This makes it possible to more easily update inspection information. Note that in step S1303, the information correction unit 208 may accept a user input concerning inspection information instead of newly issuing inspection information to be used for updating.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-074864, filed Mar. 29, 2013, which is hereby incorporated by reference herein in its entirety.

What is claimed is:

1. An imaging control apparatus comprising:
an image capturing apparatus having an image sensor;
a CPU; and
at least one memory, said CPU and said at least one memory cooperating to provide:
a reception unit configured to receive an imaging order from a RIS terminal in communication with the imaging control apparatus;
a determination unit configured to determine whether a correction should be made to the imaging order, wherein the determination unit is further configured to determine that the correction should be made in response to determining that identification information is not included in the imaging order or that the identification information included in the imaging order coincides with identification information associated with a captured image which has already been stored in a PACS terminal in communication with the imaging control apparatus, wherein the identification information identifies an image for capture in accordance with the received imaging order;
a control unit configured to permit adding identification information upon determining that the correction should be made, and to inhibit correction of the identification information upon not determining that the correction should be made;
an information obtaining unit configured to obtain identification information upon determining that the correction should be made, wherein the information obtaining unit is further configured to obtain second identification information which does not coincide with identification information associated with a captured image which has already been stored in the PACS terminal when first identification information obtained by the information obtaining unit coincides with identification information associated with a captured image which has already been stored in the PACS terminal, and wherein the information obtaining unit is further configured to determine whether the imaging control apparatus can communicate with an issuing system configured to issue identification information of an image which does not coincide with identification information associated with a captured image which has already been stored in the PACS terminal, to obtain the second identification information from the issuing system in response to determining that the imaging control apparatus can communicate with the issuing system, and to generate the second identification information in response to determining that the imaging control apparatus cannot communicate with the issuing system;
an imaging control unit configured to control the image capturing apparatus to prevent generation of an image of a subject through image capturing in accordance with the imaging order until after processing by said determination unit and said control unit; and
a storage control unit configured to send an image received by the imaging control unit and the identification information obtained by the information obtaining unit to the PACS terminal in response to the determination unit determining that the correction should be made, and send an image received by the imaging control unit and the identification information included in the imaging order received by the reception unit to the PACS terminal in response to the determination unit not determining that the correction should be made.

2. The imaging control apparatus according to claim 1, wherein the identification information is an inspection ID or an accession number of an image, and the information obtaining unit is further configured to obtain only identification information of the image such that the identification information does not coincide with any of the identification information of images stored in the PACS terminal.

3. The imaging control apparatus according to claim 1, wherein the identification information is an inspection ID or an accession number of an image, and the information obtaining unit is further configured to obtain a user input from a user repeatedly until obtaining a user input indicating identification information of the image such that the identification information does not coincide with any of the identification information of images stored in the PACS terminal.

4. The imaging control apparatus according to claim 1, wherein the received imaging order includes first identification information and does not include the second identification information, and the information obtaining unit is further configured to generate the second identification information automatically through a communication with the PACS terminal.

5. An imaging apparatus comprising the imaging control apparatus according to claim 1 and the image capturing apparatus configured to capture an image of a patient in accordance with the imaging order.

6. The imaging control apparatus according to claim 1, wherein the control unit is configured to reject identification information obtained by the information obtaining unit upon determining that the imaging order includes the identification information.

7. The imaging control apparatus according to claim 1, wherein the PACS terminal stores a plurality of captured images in association with respective identification information, and the identification information of one captured image is unique with respect to the identification information of any of the other captured images, and
the imaging control unit is further configured to control the image capturing apparatus to generate the image in accordance with the imaging order, after verifying that the identification information is included in the imaging order.

8. The imaging control apparatus according to claim 1, wherein the PACS terminal stores a plurality of captured images in association with respective identification information, and the identification information of any one of the captured images is unique with respect to the identification information of the other captured images, and
the imaging control unit is further configured to control the image capturing apparatus to generate the image in accordance with the imaging order, after verifying that the identification information included in the imaging order is different from the identification information of any of the plurality of captured images stored in the PACS terminal.

9. The imaging control apparatus according to claim 1, wherein the determination unit is further configured to further determine whether identification information obtained by the information obtaining unit coincides with identification information associated with an image already stored in the PACS terminal.

10. The imaging control apparatus according to claim 1, wherein the image sensor is comprised of a radiographic sensor and wherein the imaging control apparatus is further configured to control the image capturing apparatus to perform radiography of the subject to generate the image of the subject.

11. The imaging control apparatus according to claim 1, wherein the control unit is further configured to control a graphical user interface on a display to prompt an operator to input the identification information.

12. The imaging control apparatus according to claim 1, wherein the control unit is further configured to control a graphical user interface on a display to indicate to an operator that an input is not accepted.

13. A control method of an imaging control apparatus comprising:
receiving an imaging order from a RIS terminal in communication with the imaging control apparatus;
determining whether a correction should be made to the imaging order, wherein it is determined that the correction should be made in response to determining that identification information is not included in the imaging order or that the identification information included in the imaging order coincides with identification information associated with a captured image which has already been stored in a PACS terminal in communication with the imaging control apparatus, wherein the identification information identifies an image for capture in accordance with the received imaging order;
permitting adding identification information upon determining that the correction should be made;
inhibiting correction of the identification information upon not determining that the correction should be made;
obtaining identification information upon determining that the correction should be made, wherein second identification information which does not coincide with identification information associated with a captured image which has already been stored in the PACS terminal is obtained when obtained first identification information coincides with identification information associated with a captured image which has already been stored in the PACS terminal, wherein the second identification information is obtained by determining whether the imaging control apparatus can communicate with an issuing system configured to issue identification information of an image which does not coincide with identification information associated with a captured image which has already been stored in the PACS terminal, and by obtaining the second identification information from the issuing system in response to determining that the imaging control apparatus can communicate with the issuing system and generating the second identification information in response to determining that the imaging control apparatus cannot communicate with the issuing system;
controlling an image capturing apparatus having an image sensor, the image capturing apparatus being controlled to prevent generation of an image of a subject through image capturing in accordance with the imaging order until after processing in said determining step and in said permitting or inhibiting steps; and
sending an image received from the image capturing apparatus and the obtained identification information to the PACS terminal in response to the determination step determining that the correction should be made, and sending an image received from the image capturing apparatus and the identification information included in the imaging order received in the receiving step in response to the determination step not determining that the correction should be made.

14. A non-transitory computer-readable medium storing a program for instructing a computer to perform a method comprising:
receiving an imaging order from a RIS terminal in communication with an imaging control apparatus;
determining whether a correction should be made to the imaging order, wherein it is determined that the correction should be made in response to determining that identification information is not included in the imaging order or that the identification information included in the imaging order coincides with identification information associated with a captured image which has already been stored in a PACS terminal in communication with the imaging control apparatus, wherein the identification information identifies an image which is captured in accordance with the received imaging order;
permitting adding identification information upon determining that the correction should be made;
inhibiting correction of the identification information upon not determining that the correction should be made;

obtaining identification information upon determining that the correction should be made, wherein second identification information which does not coincide with identification information associated with a captured image which has already been stored in the PACS terminal is obtained when obtained first identification information coincides with identification information associated with a captured image which has already been stored in the PACS terminal, wherein the second identification information is obtained by determining whether the imaging control apparatus can communicate with an issuing system configured to issue identification information of an image which does not coincide with identification information associated with a captured image which has already been stored in the PACS terminal, and by obtaining the second identification information from the issuing system in response to determining that the imaging control apparatus can communicate with the issuing system and generating the second identification information in response to determining that the imaging control apparatus cannot communicate with the issuing system;

controlling an image capturing apparatus having an image sensor, the image capturing apparatus being controlled to prevent generation of an image of a subject through image capturing in accordance with the imaging order until after processing in said determining step and in said permitting or inhibiting steps; and sending an image received from the image capturing apparatus and the obtained identification information to the PACS terminal in response to the determination step determining that the correction should be made, and sending an image received from the image capturing apparatus and the identification information included in the imaging order received in the receiving step in response to the determination step not determining that the correction should be made.

* * * * *